United States Patent [19]
Aldridge et al.

[11] 4,062,876
[45] Dec. 13, 1977

[54] SENSITIVE PH INDICATOR

[75] Inventors: Clifton Aldridge, Maryland Heights, Mo.; Michael C. Meyer, O'Fallon, Ill.

[73] Assignee: McDonnell Douglas Corporation, St. Louis, Mo.

[21] Appl. No.: 682,652

[22] Filed: May 3, 1976

[51] Int. Cl.$^2$ .............................................. C09B 11/10
[52] U.S. Cl. ...................................... 260/391; 260/392
[58] Field of Search ................................ 260/391, 392

[56] References Cited
U.S. PATENT DOCUMENTS 327,953  10/1885  Kern ...................................... 260/391

Primary Examiner—Paul F. Shaver
Attorney, Agent, or Firm—Gravely, Lieder & Woodruff

[57] ABSTRACT

Process of preparing reduced aniline blue pH indicator for use in detecting presence of microorganisms in culture media. The process involves reducing aniline blue by the sequential addition of sodium thioglycollate. The reduced aniline blue indicator may be used in certain media designed for use in the cards and wells of the mechanism described in applications AUTOMATED MICROBIAL ANALYZER and MACHINE AND PROCESS FOR READING CARDS CONTAINING SPECIMENS.

5 Claims, No Drawings

SENSITIVE PH INDICATOR

BACKGROUND OF THE INVENTION

Filed on even date herewith are applications of Charles, Jones, Staples, and Wiegner entitled AUTOMATED MICROBIAL ANALYZER and MACHINE AND PROCESS FOR READING CARDS CONTAINING MEDICAL SPECIMENS which describe mechanism and apparatus suitable for analyzing specimens for specific microorganisms using a plastic tray or card which contains a series of dried culture media contained in separate but connected cells, each of the media being specific to a single organism. When the sample is inserted into the card, mixed with the media in the cells, and incubated in the machine, the organism (or organisms) present in the specimen interacts with the culture medium specific to that organism and produces a change in the medium which is read by the machine to indicate the presence of that organism. The change in the medium involves a change in the light transmitting properties of the medium, i.e., a color change or change in turbidity. The change may be caused by metabolic activity of the organism, which, for example, may cause production of acid and a change in pH which causes a color change in a pH sensitive indicator in the medium. The change in the light transmitting properties of the medium also could be caused by a precipitate forming in the medium due to metabolic activity of the organism or it could be caused by growth of the organism.

The specific media designed for use in the aforesaid cards are all designed to favor growth of one microorganism and to inhibit growth of other organisms, are capable of being freeze dried, and can function in the low $O_2$ environment of the wells of the card described in detail in said copending applications AUTOMATED MICROBIAL ANALYZER and MACHINE AND PROCESS FOR READING CARDS CONTAINING MEDICAL SPECIMENS.

In media for detection of *E. coli*, yeast and fungi, and for enumeration, the presence of each of these microorganisms is detected by metabolic activity of the organism which causes production of acid and a change in pH. Accordingly, it is an object of this invention that the pH indicator incorporated into the medium change color at the slightest change toward an acid pH so that the light transmitting properties of medium will change rapidly, thus allowing rapid detection of the microorganism sought to be identified by the mechanism in application AUTOMATED MICROBIAL ANALYZER.

In copending applications filed on even date herewith of Lanham, Rogers, and Meyer entitled E. COLI DETECTION BROTH FOR CLINICAL USE WITH AUTOMATED MICROBIAL ANALYZER; of Lanham, Wilkinson, and Dagy entitled BROTH FOR DETECTING E. COLI IN MIXED WATER SAMPLES; of Lanham, Wilkinson, and Woods entitled E. COLI IDENTIFICATION BROTH; of Meyer entitled ENUMERATION BROTH; and of Gibson and Meyer entitled BROTH FOR INDICATING PRESENCE OF CANDIDA YEAST AND OTHER FUNGI are disclosed media which utilize the reduced aniline blue of this application.

We have discovered a method of reducing the dye aniline blue so that it will change color toward acid pH, thus changing the light transmitting properties of any medium into which it is incorporated. The change in pH to which we are referring is caused by production of acid. The color of the reduced aniline blue is tan or colorless at a pH of 7.0. Upon production of acid by unknown microorganisms, the reduced aniline blue will change to blue. This change will take place within 12 to 18 hours, thus allowing rapid detection of microorganisms in clinical specimens by the mechanism of application AUTOMATED MICROBIAL ANALYZER which detects blue.

The reducing agent of the present invention is sodium thioglycollate. This reducing agent is useful in this invention because it will not inhibit growth of microorganisms, as do otherwise suitable chemical reducing agents.

SUMMARY OF THE INVENTION

This invention involves a process of reducing aniline blue so that the reduced aniline blue can operate as a highly sensitive pH indicator in culture media designed for use in the cards and wells of the mechanism described in applications AUTOMATED MICROBIAL ANALYZER and MACHINE AND PROCESS FOR READING CARDS CONTAINING MEDICAL SPECIMENS.

The reducing agent of this invention is sodium thioglycollate. This reducing agent is important since it does not inhibit growth of the microorganisms sought to be detected by the mechanism of the applications cited previously.

The reduced aniline blue indicator detects production of acid quite rapidly. Also, the indicator is resistant to errors caused by the presence of protein in culture media.

DETAILED DESCRIPTION

The aniline blue indicator of this invention is prepared by reducing aniline blue with sodium thioglycollate.

The aniline blue is water soluble, preferably from Nutritional Biochemical Co. To prepare a stock solution of aniline blue, about 4.0 to about 6.0g aniline blue should be used per 500 ml of stock solution, preferably 5.0 g per 500 ml.

Generally, aniline blue is not an especially valuable pH indicator because it responds quite slowly to pH change in reactions. Moreover, it is highly subject to error in the presence of protein.

The aniline blue has been changed by the process of the present invention by reducing and removing at least one, and possibly two amine groups. This reduction has greatly increased the speed with which aniline blue can detect changes in pH. Also, the aniline blue gives reliable results in the presence of protein.

The process of reducing the aniline blue is carried out by boiling the aniline blue in the presence of sodium thioglycollate, preferably from Nutritional Biochemical Company.

Aniline blue can be reduced by other reducing agents. However, the reduced aniline blue produced by a reduction process which employs a reducing agent other than sodium thioglycollate tends to inhibit the growth of microorganisms sought to be detected.

It is desirable that 100% of the aniline blue to be used be reduced. If less than 100% is reduced, the indicator will be unstable, i.e., it will be readily oxidized upon standing.

At a pH of 7.0 the reduced aniline blue of the present invention is tan to clear in color. Under acid conditions, reduced aniline blue changes from tan or clear to blue. This change is observed and recorded by the mechanism described in application AUTOMATED MICROBIAL ANALYZER.

Basically, the process of reducing aniline blue so that it is suitable for use as an indicator for *E. coli*, in an enumeration broth, and for *Candida* yeast and other fungi, requires the following steps:

1. Dissolving 5 g of water soluble aniline blue in a mixture comprising 100 ml 1N sodium hydroxide and 400 ml distilled water by means of stirring accompanied by slight heating;
2. Adding 7.5 g of sodium thioglycollate to the mixture of step 1, and boiling the resulting mixture for about 45 minutes while maintaining 500 ml volume.
3. Repeating step 2 with smaller amounts of sodium thioglycollate and shorter boiling times until 100% of the aniline blue is reduced.
4. Cooling the reduced aniline blue composition.
5. Adjusting the prepared solution to 500 parts by adding distilled water.

The use of excess sodium thioglycollate is not harmful to the process. The chief requirement is that 100% of the aniline blue be reduced.

The foregoing treatment causes evolution of ammonia from the aniline blue molecule, and results in a mixture of dyes which are highly pH sensitive, i.e., these dyes react within a small change in pH. The reduced aniline blue indicator begins to change color in the presence of acid. At pH 7.0 reduced aniline blue is tan to colorless. At acid condition reduced aniline blue is blue. The aniline blue fully changes color at pH of 6.4 to 6.6.

EXAMPLE I

Into a 1,000 ml graduated beaker are placed 5.0 g aniline blue, 100 ml 1N sodium hydroxide, and 400 ml distilled water. The mixture is stirred to dissolve the aniline blue. The solution is then heated slightly. 7.5 g sodium thioglycollate is added to the solution. Thereupon, the solution is heated to boiling and maintained at this temperature level for 45 minutes. 2.5 g sodium thioglycollate is added to the solution, and the solution is boiled for 10 minutes. Then 2.0 g sodium thioglycollate is added to the solution, and the solution is boiled for 3 minutes. The solution is allowed to cool. Distilled water is added until the volume reaches 500 ml. The final step should be carried out in a graduated cylinder.

What is claimed is:

1. A process for reducing aniline blue in order to make it suitable for detecting minute changes in pH comprising the steps of
   a. dissolving water-soluble aniline blue in an alkaline solution,
   b. boiling the solution of step (a) in the presence of sodium thioglycollate until the aniline blue is reduced.
2. The process of claim 1 wherein about 8 to about 12 g/l aniline blue is used.
3. The process of claim 1 wherein NaOH is used for the alkaline solution.
4. The process of claim 1 wherein about 10 to about 18 g/l sodium thioglycollate is used.
5. The process of claim 1 wherein step (b) is repeated using progressively smaller amounts of sodium thioglycollate and boiling for progressively shorter periods of time until all of the aniline blue is reduced, and thereafter cooling the reduced aniline blue solution.

* * * * *